US010758747B2

(12) United States Patent
Hofmann (10) Patent No.: US 10,758,747 B2
(45) Date of Patent: Sep. 1, 2020

(54) METHOD AND DEVICE FOR DETERMINING THE STOPPING POWER FOR PROTON THERAPY

(71) Applicant: Siemens Healthcare GmbH, Erlangen (DE)

(72) Inventor: Christian Hofmann, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/242,149

(22) Filed: Jan. 8, 2019

(65) Prior Publication Data
US 2019/0209865 A1 Jul. 11, 2019

(30) Foreign Application Priority Data
Jan. 10, 2018 (EP) .................... 18150964

(51) Int. Cl.
*A61N 5/10* (2006.01)
(52) U.S. Cl.
CPC ........... *A61N 5/1048* (2013.01); *A61N 5/103* (2013.01); *A61N 5/1039* (2013.01);
(Continued)

(58) Field of Classification Search
None
See application file for complete search history.

(56) References Cited

U.S. PATENT DOCUMENTS

2009/0274269 A1* 11/2009 Foland .................. A61N 5/1048
378/54
2010/0303196 A1* 12/2010 Zou ....................... A61B 6/032
378/5

(Continued)

FOREIGN PATENT DOCUMENTS

CN 101897595 A 12/2010
CN 106880902 A 6/2017

OTHER PUBLICATIONS

Han et al. "A linear, separable two-parameter model for dual energy CT imaging of proton stopping power computation" Med. Phys. 43 (1), Jan. 2016 (Year: 2016).*
Hünemohr et al. ("Ion range estimation by using dual energy computed tomography" Z Med Phys. Dec. 2013;23(4):300-13 (Year: 2013).*
European Search Report for corresponding Application No. 18150964. 7-1124 filed Aug. 1, 2018, with translation.
Hünemohr, Nora et al. "Ion range estimation by using dual energy computed tomography" Zeitschrift für Medizinische Physik, vol. 23, No. 4, pp. 300-313, Dec. 2013.

(Continued)

*Primary Examiner* — James Choi
(74) *Attorney, Agent, or Firm* — Lempia Summerfield Katz LLC (57) ABSTRACT

A method is provided for determining the stopping power from computed tomography scans. The method includes preparing computed tomography scans of a body region with two different recording energies; determining the stopping power for different CT numbers from dual energy image areas of the computed tomography scans; forming a data field in which the determined values for the stopping power for different CT numbers from dual energy image areas are applied as a function of the CT numbers; forming a look-up table from the data field; determining the stopping power for different CT numbers from single energy image areas of the computed tomography scans by the look-up table. A corresponding device and control device, a corresponding particle therapy system, and a corresponding computed tomography system, are also provided.

14 Claims, 4 Drawing Sheets

(52) U.S. Cl.
CPC .......... *A61N 5/1043* (2013.01); *A61N 5/1081* (2013.01); *A61N 2005/1052* (2013.01); *A61N 2005/1061* (2013.01); *A61N 2005/1074* (2013.01); *A61N 2005/1087* (2013.01)

(56) References Cited

U.S. PATENT DOCUMENTS

| | | | |
|---|---|---|---|
| 2011/0122997 A1* | 5/2011 | Lu ........................ | A61N 5/1031 378/65 |
| 2011/0220794 A1* | 9/2011 | Censor ................. | G01N 23/046 250/307 |
| 2017/0172533 A1 | 6/2017 | Raupach | |

OTHER PUBLICATIONS

Hünemohr, Nora et al. "Experimental verification of ion stopping power prediction from dual energy CT data in tissue surrogates" Physics in Medicine and Biology, vol. 59, pp. 83-96, 2014.

Möhler, Christian et al. "Experimental verification of stopping-power prediction from single- and dual-energy computed tomography in biological tissues" Physics in Medicine and Biology, vol. 63, No. 2, Jan. 2018.

Chinese Office Action for related Chinese Patent Application No. 201910011161.3, dated Nov. 18, 2019, with English translation.

\* cited by examiner

METHOD AND DEVICE FOR DETERMINING THE STOPPING POWER FOR PROTON THERAPY

The present patent document claims the benefit of European Patent Application No. EP 18150964.7, filed Jan. 10, 2018, which is also hereby incorporated by reference.

TECHNICAL FIELD

The disclosure relates to a method and a device for determining the stopping power for particle therapy, in particular, for proton therapy. The disclosure furthermore relates to a corresponding control device for a computed tomography system and a computed tomography system including such a control device.

BACKGROUND

Nowadays, the stopping power ("SPR" for "Stopping Power Ratio") of protons for the treatment planning of proton therapy may be obtained from single energy data of a computed tomography scan. The term "single energy" relates to the manner of computed tomography scan with only a single recording energy. So-called "CT values" are determined for the individual voxels from the reconstructed computed tomography scan or its raw data. These CT values are then assigned SPR values, that is to say, values which reproduce the stopping power. The nature of the CT values, which are also referred to as hereinafter as "CT numbers", is known to the person skilled in the art in this field. The CT numbers may be in Hounsfield units H.

The assignment of SPR values to CT numbers may be achieved by a look-up table or "Hounsfield look-up table" (HLUT). Based on calibration measurements, such a look-up table is generated for single energy data which assigns a CT value a discrete SPR value.

Such calibration measurements are disadvantageous as they imply an additional expense and an additional potential source of error.

Figure 1:
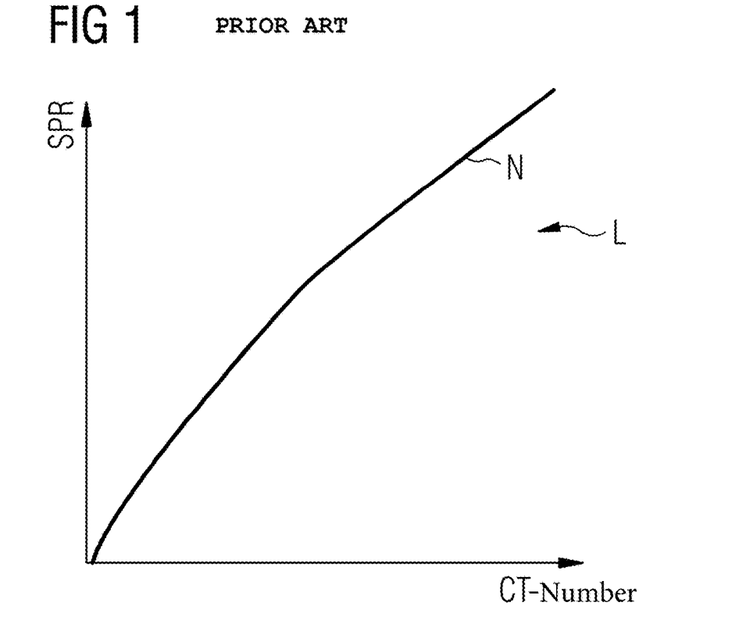
FIG. 1 depicts a diagrammatic view of a look-up table according to the prior art.

It is common practice, depending on the treatment, to generate different look-up tables, e.g., one for treatments of the head and one for treatments of the body. An exemplary look-up table is shown in FIG. 1.

Recently, the use of dual energy CT images ("DECT") was discovered as an alternative to the previous approach. The term "dual energy" likewise refers to the manner of the recording principle with two different recording energies. According to this principle, the spectral information of the dual energy data is used to determine the stopping power SPR with which SPR values may be directly calculated from CT numbers (see, for example, "Ion Range estimation by using dual energy computed tomography"; N. Hünemohr et. al.; Z. Med. Phys. 23 (2013) pp. 300-313 or "Experimental verification of ion stopping power prediction from dual energy CT data in tissue surrogates"; N. Hünemohr et. al.; Phys. Med. Biol. 59 (2014) pp. 83-96).

There are dual energy CT systems on the market which record the images with high and low energy with two different fields of view ("FOV"). The consequence of this is a spatial limitation of the prediction for the SPR as dual energy data is only possible within the smaller field of view (FOV).

This spatial limitation is disadvantageous for the treatment planning of proton therapy as calibration data is scanned again for those regions for which only single energy data is available, resulting in the aforementioned disadvantages.

SUMMARY AND DESCRIPTION

It is an object of the present disclosure to provide an alternative, more convenient method and a corresponding device and furthermore to provide a control device for controlling a computed tomography system or a particle therapy system and a corresponding computed tomography system or particle therapy system with which the aforementioned disadvantages are avoided.

This object is achieved by a method, a device, a control device, a computed tomography system, or a particle therapy system as described herein.

The scope of the present disclosure is defined solely by the appended claims and is not affected to any degree by the statements within this summary. The present embodiments may obviate one or more of the drawbacks or limitations in the related art.

The method serves to determine the stopping power ("SPR") from computed tomography scans for the technical field of particle therapy, in particular of proton therapy. The method includes the following acts.

In one act, computed tomography scans are provided. This provision includes both the provision of existing computed tomography scans and the production of new computed tomography scans, that is to say, for example a direct recording by a CT scanner. As the scan was made with two recording energies, the computed tomography scans are also described as "dual energy CT scans" (DECT scans). For recording, for example, two image recording devices of a CT scanner may be swiveled around the body region at an angular range of at least 90° or at least 180°, and produce a number of multiple images in the process.

The computed tomography scans represent a body region and, due to the different fields of view ("FoV") for different recording energies, partially contain visual information about two different recording energies with which this body region has been scanned. These regions are described as "dual energy image areas," in contrast to those areas in which, due to the different fields of view, only information for a single recording energy is available. These are described as "single energy image areas."

The (reconstructed) scans may include information about CT numbers so that as a rule a CT number is assigned to each voxel. Should this not be the case because only raw data of a CT are available for the method, for example, the CT numbers H in this act would be calculated from the image data of the computed tomography scans at the same time. This may occur in a case, for example, in which the attenuation coefficient $\mu$ of a voxel and the attenuation coefficient of water $\mu_W$ and of air $\mu_L$ is known with the formula $$H = \frac{\mu - \mu_W}{\mu_W - \mu_{Luft}} \cdot 1000 \text{ HU}, \qquad (1)$$

wherein the factor 1000 is used as a rule, but theoretically factors with another value may also be used. To simplify matters, a $\mu_L$ with the value=0 may also be assumed.

In another act, the stopping power $SPR_{DE}$ (the dual energy stopping power or duel energy image area stopping power) is determined. In this act, the stopping power $SPR_{DE}$ for different CT numbers H is determined from dual energy image areas of the computed tomography scans, hence those image areas in which image data with both recording energies is present. The calculation acts for determining the stopping power $SPR_{DE}$ from DECT data are well known, wherein a plurality of possible avenues exist. Nevertheless, a concrete example for each of these avenues is so complex that it would go beyond the scope of this description. Therefore, reference is only made here to the prior art for the determination of stopping power SPR from DECT data, for example, to the publications referred to in the introduction.

In another act, a data field is formed. The values determined in the previous act for the stopping power $SPR_{DE}$ for different CT numbers H from dual energy image areas are applied as a function of the CT numbers H in a data field. As a rule, the data field does not contain a single value for the stopping power $SPR_{DE}$ for a single CT number. If this application includes bins which are filled with the values, as a rule a distribution of values is obtained which may have an extreme value. If the stopping power $SPR_{DE}$ has been determined using the well-known method, as a rule the extreme value is a maximum.

In another act, a look-up table is formed. The look-up table is formed from the data field obtained in the previous act. Such a look-up table is also described as HLUT ("Hounsfield Look Up Table"). No calibration measurements are necessary for the formation of the look-up table. It has been recognized within this disclosure that the look-up table may be formed directly from the data field. Concrete examples for the formation of the look-up table are described in more detail below.

In another act, the stopping power $SPR_{SE}$ (the single energy stopping power or single energy image area stopping power) is determined. With the look-up table obtained from the previous act it is now possible to determine the stopping power $SPR_{SE}$ for different CT numbers H from single energy image areas of the computed tomography scans, that is to say, the areas in which image data is present with only a single recording energy. In a direct CT scan, the stopping power $SPR_{SE}$ may thus also be specified by the method in real time for single energy image areas.

A device for the determination of stopping power SPR from computed tomography scans includes the following components.

The device includes an interface for the receipt of computed tomography scans of a body region with two different recording energies. In the event that these computed tomography scans do not include any CT numbers as, for example, they exist as raw data, it is advantageous if this interface includes a unit which may determine these CT numbers from the image data, for example, an image reconstruction unit.

The device also includes a first determination unit for determining the stopping power $SPR_{DE}$ for different CT numbers H from dual energy image areas of the computed tomography scans, as has already been explained in more detail above.

The device also includes a computing unit for the formation of a data field in which the determined values for the stopping power $SPR_{DE}$ are applied as a function of the CT numbers H for different CT numbers H from dual energy image areas, as has also been explained in more detail previously.

The device also includes a look-up table module for the formation of a look-up table from the data field.

The device also includes a second determination unit for determining the stopping power $SPR_{SE}$ for different CT numbers H from single energy areas of the computed tomography scans by the look-up table.

A control device for controlling a computed tomography system or a particle therapy system, in particular proton therapy system, is designed to perform the method and/or includes the device described herein.

A computed tomography system includes a control device.

A particle therapy system, in particular proton therapy system, includes a control device.

A majority of the aforementioned components of the device or the control device may be implemented wholly or in part in the form of software modules in a processor of a computer system or a corresponding control device. A largely software-based implementation has the advantage that computer systems or control devices already used hitherto may also be upgraded by a software update to operate in the manner as described herein. Insofar, the object is also achieved by a corresponding computer program product with a computer program which may be loaded directly into a storage device of a computer system or a control device, with program segments to execute all the acts of the method when the program is executed in the computer system or the control device. Besides the computer program, if applicable, such a computer program product may also include additional components such as, for example, documentation and/or additional components as well as hardware components, such as hardware keys (e.g., dongles, etc.), for use of the software.

For transport to the computer system or to the control device and/or to the storage on or in the computer system or the control device, a computer-readable medium, for example, a memory stick, a hard disk or another portable or permanently installed data carrier may be used on which the program segments of the computer program readable and loadable from the computer system or a computer unit of the control device are stored. The computer unit may have one or more cooperating microprocessors or the like for this purpose.

Further particularly advantageous embodiments and developments will emerge from the following description, wherein the claims of a claim category may also be developed analogously to the claims and description parts of another claim category and in particular individual features of various exemplary embodiments and/or variants may also be combined to form new exemplary embodiments and/or variants.

The data field may be formed such that the data field exists as a point cloud, whereby a two-dimensional distribution of values is meant. In one data field in which the horizontal axis indicates the CT number H and the vertical axis the stopping power SPR, the determined values of the stopping power $SPR_{DE}$ from the double energy data are available as a two-dimensional value distribution (e.g., point cloud) in the data field. The point cloud may have a density distribution.

In the example that the values are applied in the form of a two-dimensional histogram, as a rule the CT value H corresponds to the column and the value for the stopping power SPR to the row of a field with discrete coordinates (x, y) which constitute bins. In this case, the points are present in the form of a frequency distribution. This means that for a column of the aforementioned discrete field (a CT number), a frequency distribution of stopping power calculated for this CT value exists. The totality of all the values of the data field therefore produces a point cloud which constitutes a two-dimensional frequency distribution.

A function is fitted into this point cloud. The adaptation of a function is known to a person skilled in the art and is also described as an "adjustment computation" or as a "curve fit". For example, the Gauss-Newton method may be used for fitting the function into the point cloud.

The function indicates a discrete value for the stopping power $SPR_L$ for a CT number, in other words corresponds to a function $SPR_L$ (CT number). The function thus defines direct values of a look-up table. This look-up table may exist in the form of a tangible table in which an SPR value may be directly read off for each CT number. In this regard, the function F would only constitute one way of preserving the values. In another instance, a graph on which the SPR value may be read off in a diagram may also constitute the look-up table. Finally, in automatic processing the function may also constitute the look-up table as this assigns every CT number an SPR value.

If a CT number initially exists, this may be directly converted into a value for the stopping power $SPR_L$ by the function, wherein in the event that CT numbers from points from single energy image areas of the computed tomography scans are used, $SPR_L = SPR_{SE}$ applies.

In this sense, in one exemplary device, the computing unit is designed to form a data field in the form of a point cloud, in particular in the form of a two-dimensional histogram and the look-up table module is designed to adapt a function to the point cloud, wherein the function defines values of the look-up table.

The location-dependent stopping power SPR (x, y, z) may be determined for a number of voxels, in particular for all the voxels, of a computed tomography scan. This is done either by direct calculation for dual energy image areas or by the look-up table for single energy image areas. This may be achieved by adopting the position information in the calculation of the stopping power SPR for the relevant voxels which have a known image position (x, y, z). The Z-coordinate is not crucial for two-dimensional image data but highly advantageous for three-dimensional image data. When applying the stopping power SPR (x, y, z) at the corresponding coordinates, an image is produced with visual information which directly indicates the stopping power for each point of the recorded body region. Here, SPR may correspond to the value $SPR_{DE}$ or $SPR_{SE}$ depending on the image area.

Different look-up tables may be created for different diameters of recorded regions. Thus, effects based on beam hardening may be compensated, which significantly improves the accuracy of the determination of values for the stopping power for different body regions. For example, different look-up tables may be determined for predetermined diameters, (e.g., 10 cm, 20 cm, 30 cm, 40 cm, and so on).

The relevant diameter may be determined or estimated from the relevant computed tomography scans for these look-up tables. An appropriate estimate of the diameter of an object shown in a cross section may be achieved with a differential evolution algorithm.

To determine a value for the stopping power $SPR_{SE}$ for a CT number in the single energy range, the diameter in this region may be estimated (for example, with the aforementioned algorithm) and the value to be adopted in the present case determined for the stopping power $SPR_{SE}$ from a linear interpolation of the functions (or look-up values) of the aforementioned look-up tables of adjacent diameters. If, for example, the value for the stopping power $SPR_{SE}$ in a single energy range is to be determined at one point of the leg for which a diameter of 15 cm has been estimated, those with a diameter of 10 cm and a diameter of 20 cm would be selected as adjacent from the aforementioned look-up tables and their respective functions (or look-up values) adjusted to the diameter of 15 cm by linear interpolation. Of course, scanning in increments finer than 10 cm is also possible, wherein the linearly interpolated values become ever more accurate with increasingly fine scanning.

A correction of beam hardening may take place before determination of the values of the stopping power $SPR_{DE}$. Dedicated calibrations may be done for this purpose to produce dedicated look-up tables. This has the advantage of already enabling compensation for the spectral effect of beam hardening on the recorded images before the stopping power is determined.

In the case of adjoining dual energy and single energy image areas, the weighting of the influence of the stopping power $SPR_{DE}$ of the dual energy image area and the stopping power $SPR_{SE}$ of the single energy image area may be determined. This may take place in a predetermined transition area with a thickness $\Delta$ by a predetermined transition function w(r) with $0 < r < \Delta$. The value r constitutes a spatial measurement of part of the thickness. This may be a simple measurement (in mm or picture elements, e.g., pixels or voxels) or a fraction of the thickness.

To this end, an effective stopping power $SPR_{Eff}$ may be determined over the entire transition area from the stopping power $SPR_{DE}$ of the dual energy image area and the stopping power $SPR_{SE}$ of the single energy image area. This may take place according to the formula:

$$SPR_{Eff}(r) = w(r) \cdot SPR_{DE} + (1 - w(r)) \cdot SPR_{SE}. \quad (2)$$

The transition function w(r) may be selected for a linear transition with $w(r) = \Delta - r$.

BRIEF DESCRIPTION OF THE DRAWINGS

The disclosure is explained again in more detail hereinafter with reference to the attached figures on the basis of exemplary embodiments. In the various figures, the same components have identical reference numerals. The figures are not to scale as a rule. In the diagrams.

DETAILED DESCRIPTION

FIG. 1 depicts a diagrammatic view of a look-up table L according to the prior art as already explained in the introductory part. Based on calibration measurements, a look-up table L for single energy data is generated. The look-up value curve N assigns each CT value an SPR value at a specific interval.

Figure 2:
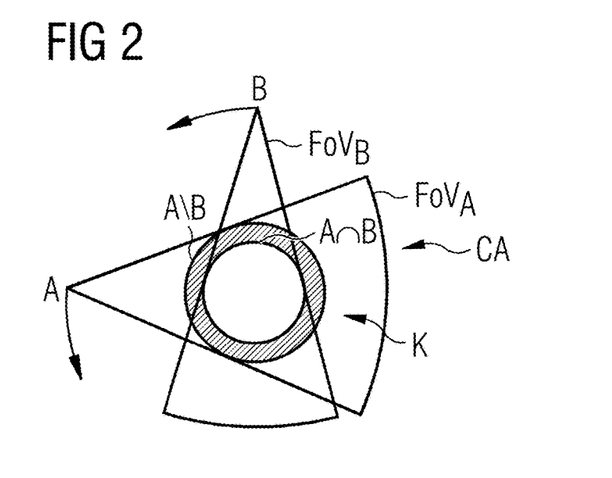
FIG. 2 depicts an example of a view of a computed tomography scan with two energies and two fields of view FoV.

FIG. 2 depicts a view of a computed tomography scan CA with two recording energies A, B and two fields of view $FoV_A$, $FoV_B$. During recording, the two fields of view $FoV_A$, $FoV_B$ indicated as cones rotate around a determined angular range, (e.g., 180°), and in the process, record the body region K, which is shown here as a circle. The field of view $FoV_A$ of the recording energy A scans a larger area of the body region K than the field of view $FoV_B$ of the recording energy B. Image data with both recording energies A, B is present in the inner part of the circle, the dual energy image area A∩B, and image data with only a single recording energy A is present in the outer part of the circle, the single energy image area (A\B).

Figure 3:
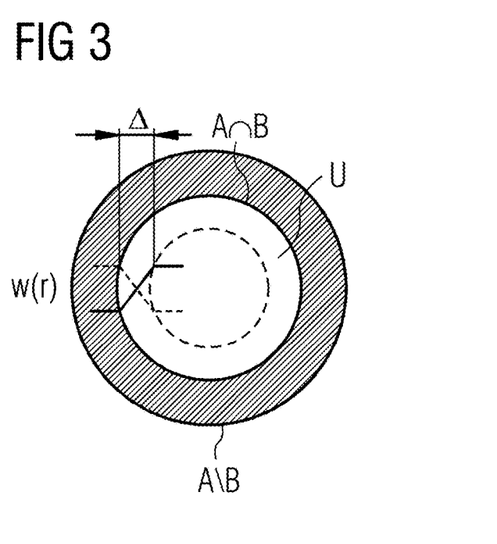
FIG. 3 depicts an example of an outline of the transition area.

FIG. 3 serves to clarify the transition area U. The two circular areas of FIG. 2 corresponding to the dual energy image area A∩B (inside) and the single energy image area A\B (outside) are shown again here. At the point where these two areas are adjacent, a discontinuity, a "jump", would be identifiable in the subsequent data regarding the stopping power $SPR_{DE}$ and $SPR_{SE}$. To compensate for this discontinuity of the data, a transition function w(r) may be employed.

The transition area U is here located inside the dual energy image area A∩B (edge of the dashed circle to the edge of the white circle) and has a width Δ. If r is a number between 0 and Δ, this transition function w(r) may determine the weighting of the influence of the CT numbers of the dual energy image area A∩B and the single energy image area A\B on the determined effective stopping power $SPR_{Eff}$.

The effective stopping power $SPR_{Eff}$ may, according to the formula $SPR_{Eff}(r)=w(r) \cdot SPR_{DE}+(1-w(r)) \cdot SPR_{SE}$, be calculated with the stopping power $SPR_{DE}$ and $SPR_{SE}$ and the transition function w(r). For example, $w(r)=r-\Delta$ may be adopted as a simple transition function w(r) which produces a linear transition, as indicated here. The influence of $SPR_{DE}$ declines in a linear fashion outwardly and the influence of $SPR_{SE}$ increases in a linear fashion outwardly.

Figure 4:
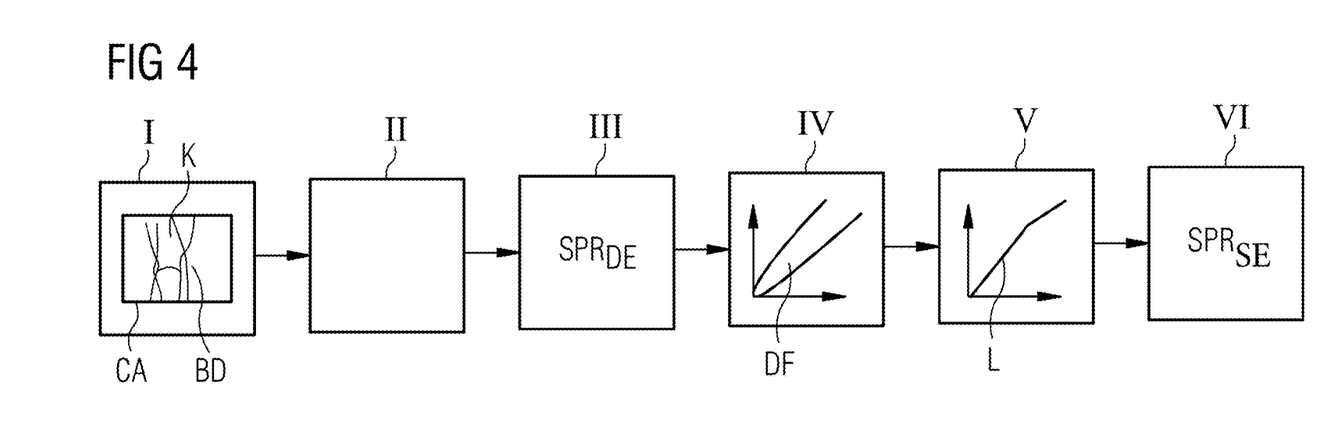
FIG. 4 depicts a diagrammatic block diagram of the method according to an example.

FIG. 4 depicts a diagrammatic block diagram of the method for determining the stopping power SPR from computed tomography scans CA. The method includes the following acts.

In act I, computed tomography scans CA of a body region K are provided. This may also mean the production of scans. The computed tomography scans CA are produced or provided with two different recording energies A, B. The scans may take place as outlined in FIG. 2.

In act II, which is an optional act, a calculation of CT numbers H from image data BD of the computed tomography scans CA is undertaken. This act may be necessary if the aforementioned computed tomography scans CA are made available to the method in the form of raw data and firstly an image reconstruction takes place, as is explained in more detail, for example, in the context of FIG. 6.

In act III, the stopping power $SPR_{DE}$ is determined for different CT numbers H from dual energy image areas A∩B of the computed tomography scans CA, in other words, in those image areas in which image data DB with both recording energies A, B is present.

In act IV, a data field DF is formed in which the determined values for the stopping power $SPR_{DE}$ for different CT numbers H from dual energy image areas A∩B are applied as a function of the CT numbers H.

In act V, a look-up table L is formed, for example, in the form of a Hounsfield look-up table (HLUT), from the data field DF. This may be achieved, for example in a data field DF which exists as a point cloud, by adapting ("fitting") a function F to the extremes of the point cloud. This function F then determines the values of the look-up table L.

In act VI, the stopping power $SPR_{SE}$ for different CT numbers H is determined from single energy image areas A\B of the computed tomography scans CA, that is to say, the image areas in which image data SB with a single recording energy A, B is present, from the look-up table L.

Figure 5:
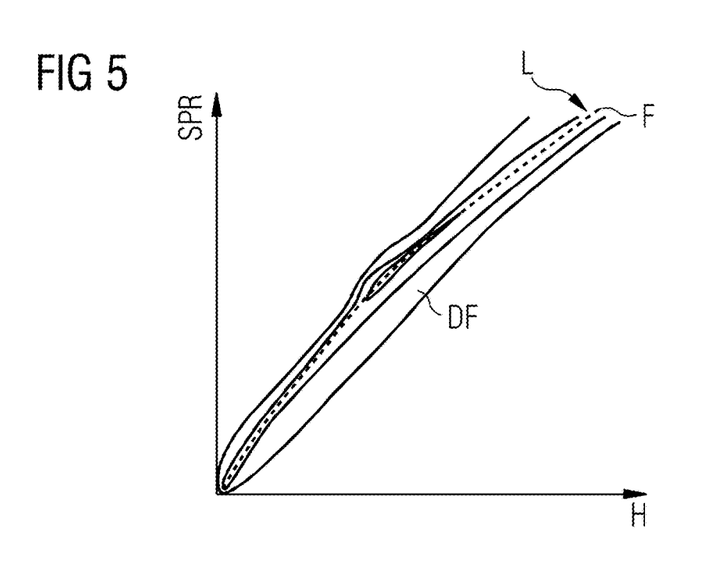
FIG. 5 depicts an example of a data field and a look-up table.

FIG. 5 depicts a data field DF produced by the method in which the solid lines are intended to indicate a point cloud of differing intensity. A function F (dashed line), which defines the look-up table L, is fitted into this point cloud.

Figure 6:
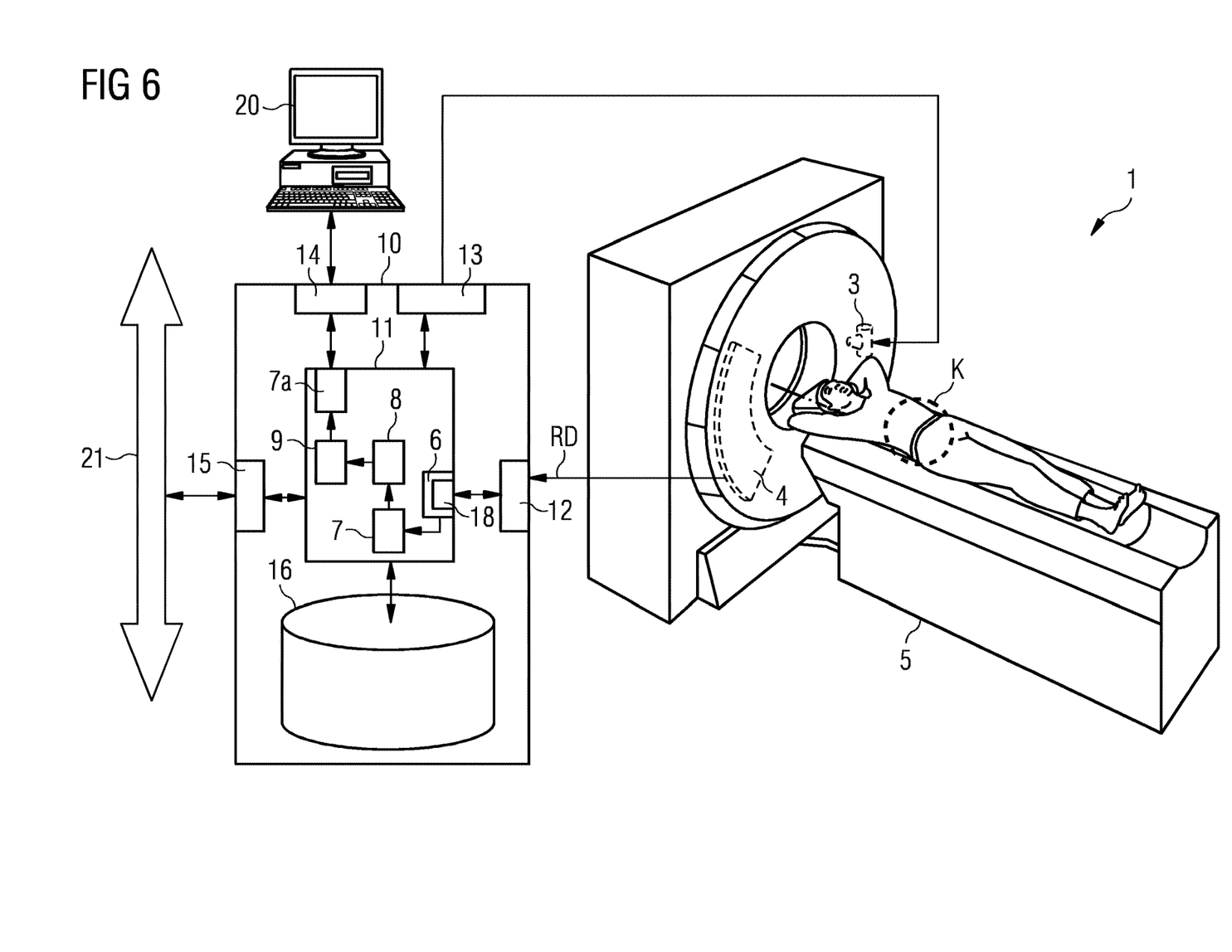
FIG. 6 depicts a diagrammatic view of an imaging system with an exemplary embodiment of a control device for the execution of the method.

FIG. 6 depicts a roughly diagrammatic view of a computed tomography system 1 with a control device 10 for the performance of the method. In certain examples, the computed tomography system 1 has a scanner 2 with a gantry in which an X-ray source 3 rotates, which irradiates a patient who is pushed into a measuring area of the gantry by a couch 5 so that the radiation impinges on a respective detector 4 opposite the X-ray source 3.

The computed tomography system 1 is designed to record dual energy scans. It is possible that the X-ray source 3 may generate radiation with two different energies or a second X-ray source (not shown here) with a second detector is present, for example at an angle of 90° to the aforementioned X-ray source 3. Furthermore, it is assumed that the two scans of different recording energy A, B take place with different fields of view $FoV_A$, $FoV_B$ (see FIG. 2).

It is explicitly pointed out that the exemplary embodiment according to FIG. 6 is only an example of a CT and other CT constructions may be used, for example, with a ring-shaped fixed X-ray detector and/or a plurality of X-ray sources.

Likewise, only the components which are helpful for the description of the disclosure are shown in the control device 10. In principle, such CT systems and associated control devices are known to a person skilled in the art and therefore do not need to be explained in detail.

Here, a core component of the control device 10 is a processor 11 on which various components are implemented in the form of software modules. The components shown in the processor 11 correspond to the components of the device 11.

Furthermore, the control device 10 has a terminal interface 14 to which a terminal 20 is connected, by way of which an operator may operate the control device 10 and thus the computed tomography system 1. A further interface 15 is a network interface for connection to a data bus 21 in order to establish a connection to an Radiology Information System (RIS) or Picture Archiving and Communication System (PACS).

The scanner 2 may be controlled by the control device 10 by way of a control interface 13, e.g., the rotation speed of the gantry, the displacement of the patient couch 5 and the X-ray source 3 itself, for example, are controlled. The raw data RD are read out from the detector 4 via an acquisition interface 12. Moreover, the control device 10 has a storage unit 16 in which, for example, control or measurement protocols may be stored.

An interface 6 for receiving the computed tomography scans CA of a body region K with two different recording energies A, B is embodied on the processor 11 as a software component. In this example, the interface receives raw data RD, which is first prepared. For this purpose, an image data reconstruction unit 18 is implemented in the interface 6 with which the desired image data is reconstructed from the raw data RD obtained via the data acquisition interface 12. This image data reconstruction unit 18 processes the raw data such that the resulting image data corresponds to the CT numbers H or at least contains these.

The reconstructed computed tomography scans CA are forwarded to a first determination unit 7. This determines the stopping power $SPR_{DE}$ for different CT numbers H from dual energy image areas A∩B of the computed tomography scans CA.

The determined data is forwarded to a computing unit 8. This forms a data field DF in which the determined values for the stopping power $SPR_{DE}$ for different CT numbers H from dual energy image areas (A∩B) are applied as a function of the CT numbers H.

From this data field DF, a look-up table module 9 creates a look-up table L.

Finally, a second determination unit 7a determines the stopping power $SPR_{SE}$ for different CT numbers H from single energy areas A\B of the computed tomography scans CA from the look-up table.

The determined values for the respective stopping powers $SPR_{DE}$ and $SPR_{SE}$ may then be output on the terminal 20, be stored in the storage unit 16 or be made available to other devices by the data bus 21 or stored in a network storage unit.

Figure 7:
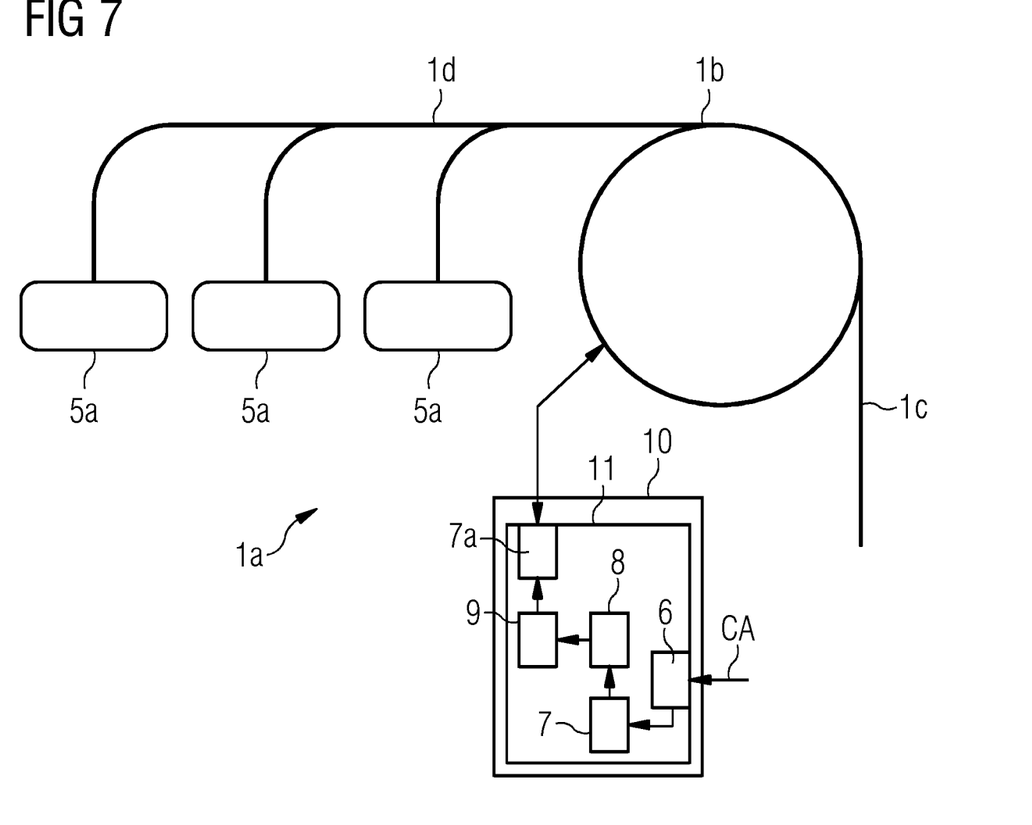
FIG. 7 depicts a diagrammatic view of a particle therapy system with an exemplary embodiment of a control device for the execution of the method.

FIG. 7 depicts a roughly diagrammatic view of a particle therapy system 1a with an exemplary embodiment of a control device 10 for execution of the method. The particle therapy system 1a is here shown as an accelerator system and includes three treatment places 5a. By way of the beamline 1c shown on the right of the figure, pre-accelerated particles, for example protons, are introduced into an accelerator ring 1b, there accelerated to terminal velocity and if necessary, stored. The particles are directed to the treatment places 5a by way of an extraction beamline 1d and are there available for the treatment of patients.

The particle energy is precisely controlled so that the particle energy develop their maximum effect at a clearly defined place in the patient. The stopping power in the corresponding body region K of the patient is an important measurement for the determination of this energy.

The control device 10 in the processor 11 of which the device is formed, as already explained in more detail in FIG. 6, for example controls the energy of the accelerator ring 1b and extraction by way of the extraction beamline 1d. The device in the processor 11 may determine the stopping power in the relevant body region K from appropriate computed tomography scans CA and the control device 10 determine the appropriate accelerator energy from this stopping power and control the accelerator accordingly. It may be advantageous if the stopping power is known as precisely as possible. The more precisely the stopping power may be determined, the more precise the planning, which directly affects the effectiveness of the radiation.

It is finally pointed out again that the method previously described in detail and the computed tomography system 1 shown and the particle therapy system 1a are only exemplary embodiments which may be modified by a person skilled in the art in a variety of ways without departing from the scope of the disclosure. Furthermore, the use of the indefinite article "a" or "an" does not exclude the possibility of the relevant features also being present multiple times. Likewise, the terms "unit" and "module" do not exclude the relevant components from including a plurality of interacting subcomponents which may, if necessary, also be spatially distributed.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for determining a stopping power from computed tomography (CT) scans, the method comprising:
   receiving CT scans of a body region from a CT system having a scanner and an X-ray source, the CT scans comprising a first CT scan having a first recording energy for a first field of view and a second CT scan having a second, different recording energy for a second, different field of view, wherein the first field of view and the second field of view overlap a first part of the body region to provide an overlapping area, wherein the first field of view and the second field of view do not overlap a second part of the body region to provide a non-overlapping area, wherein the non-overlapping area is covered by one field of view of the first or second field of view but not the other field of view, and wherein a dual energy image area is defined by the overlapping area and a single energy image area is defined by the non-overlapping area;
   determining a dual energy stopping power for different CT numbers from the dual energy image area;
   forming a data field in which determined values for the determined dual energy stopping power for the different CT numbers from the dual energy image area are applied as a function of the different CT numbers from the dual energy image area;
   forming a look-up table from the data field;
   determining a single energy stopping power for different CT numbers from the single energy image area by the look-up table.

2. The method of claim 1, wherein the data field exists as a point cloud and a function which defines values of the look-up table is configured to the point cloud.

3. The method of claim 2, wherein the data field is in a form of a histogram.

4. The method of claim 1, wherein a location-dependent dual energy stopping power and/or single energy stopping power is determined for a number of voxels of a CT scan with known image position.

5. The method of claim 1, wherein different look-up tables are created for different diameters of scanned regions.

6. The method of claim 5, wherein, in the determining of the single energy stopping power for a CT number in the single energy image area, a diameter in the single energy image area is estimated and the single energy stopping power results from a linear interpolation of look-up tables.

7. The method of claim 5, wherein relevant diameters for a look-up table are determined or estimated from a region depicted in an associated CT scan.

8. The method of claim 7, wherein, in the determining of the single energy stopping power for a CT number in the single energy image area, a diameter in the single energy image area is estimated and the single energy stopping power results from a linear interpolation of look-up tables.

9. The method of claim 1, wherein, before the determining of the values of the dual energy stopping power, a beam hardening correction takes place.

10. The method of claim 9, wherein at least one dedicated calibration takes place to generate a dedicated look-up table for the beam hardening correction.

11. The method of claim 1, wherein in a case of the dual energy image area and the single energy image area adjoining in a predetermined transition area with a thickness Δ, an effective stopping power is calculated from the dual energy stopping power of the dual energy image area and the single energy stopping power of the single energy image area and a predetermined transition function w(r) with location parameter r, with 0<r<Δ.

12. The method as claimed in claim 11, wherein the effective stopping power is calculated with the dual energy stopping power, the single energy stopping power, and a transition function w(r) according to the formula:

$$SPR_{\mathit{Eff}}(r)=w(r)\cdot SPR_{DE}+(1-w(r))\cdot SPR_{SE}.$$

13. A device for determining a stopping power from computed tomography (CT) scans, the device comprising:
an interface configured to receive CT scans of a body region from a CT system having a scanner and an X-ray source, the CT scans comprising a first CT scan having a first recording energy for a first field of view and a second, different recording energy for a second, different field of view, wherein the first field of view and the second field of view overlap a first part of the body region to provide an overlapping area, wherein the first field of view and the second field of view do not overlap a second part of the body region to provide a non-overlapping area, wherein the non-overlapping area is covered by one field of view of the first or second field of view but not the other field of view, and wherein a dual energy image area is defined by the overlapping area and a single energy image area is defined by the non-overlapping area; and
a processor configured to:
determine a dual energy stopping power for different CT numbers from the dual energy image area;
form a data field in which determined values for the dual energy stopping power for the different CT numbers from the dual energy image area are applied as a function of the CT numbers from the dual energy image area;
form a look-up table from the data field; and
determine a single energy stopping power for different CT numbers from the single energy image area by the look-up table.

14. A computed tomography or particle therapy system comprising:
a scanner;
an X-ray source; and
a control device configured to:
receive computed tomography (CT) scans of a body region from the scanner and the X-ray source, the CT scans comprising a first CT scan having a first recording energy for a first field of view and a second CT scan having a second, different recording energy for a second field of view, wherein the first field of view and the second field of view overlap a first part of the body region to provide an overlapping area, wherein the first field of view and the second field of view do not overlap a second part of the body region to provide a non-overlapping area, wherein the non-overlapping area is covered by one field of view of the first or second field of view but not the other field of view, and wherein a dual energy image area is defined by overlapping areas for the first and second fields of view and a single energy image area is defined by the non-overlapping area;
determine a dual energy stopping power for different CT numbers from the dual energy image area;
form a data field in which determined values for the dual energy stopping power for the different CT numbers from the dual energy image area are applied as a function of the CT numbers from the dual energy image area;
form a look-up table from the data field; and
determine a single energy stopping power for different CT numbers from the single energy image area by the look-up table.

* * * * *